United States Patent [19]

Hawkins et al.

[11] Patent Number: 4,799,495
[45] Date of Patent: Jan. 24, 1989

[54] LOCALIZATION NEEDLE ASSEMBLY

[75] Inventors: Irwin F. Hawkins; George A. Rafferty, Jr., both of Gainesville; Mark C. Hawkins; Jeffrey S. Hawkins, both of Micanopy, all of Fla.

[73] Assignee: National Standard Company, Niles, Mich.

[21] Appl. No.: 28,609

[22] Filed: Mar. 20, 1987

[51] Int. Cl.⁴ ............................................. A61B 10/00
[52] U.S. Cl. ...................................... 128/754; 604/164
[58] Field of Search .................. 128/330, 340, 329 R, 128/339, 751, 753, 754; 604/164–169

[56] References Cited

U.S. PATENT DOCUMENTS

| 3,308,819 | 3/1967 | Arp | 604/164 |
| 4,517,965 | 5/1985 | Ellison | 128/754 |
| 4,592,356 | 6/1986 | Gutierrez | 128/339 |
| 4,682,606 | 7/1987 | De Caprio | 128/754 |

Primary Examiner—Dalton L. Truluck
Assistant Examiner—Denise Whelton
Attorney, Agent, or Firm—Emrich & Dithmar

[57] ABSTRACT

A localization needle assembly includes an outer tubular cannula and an inner needle slidably mounted for movement within the outer cannula between extended and retracted portions, the needle having a pointed tip which projects from the front end of the assembly when the needle is extended while the surgeon locates a lesion. When the tip is retracted, a barb, which is secured to the needle, is deployed through an opening in the sidewall of the outer cannula when the needle is retracted, the barb anchoring the needle assembly in body tissue in the proximity of the lesion. Detachable handles are provided for locking the inner needle and outer cannula together and to facilitate extension and retraction of the needle. In one embodiment, the outer cannula has a helical screw tip for securing the needle assembly to a body organ or body tissue. A guide assembly is advanced along the needle assembly which has been inserted into the body tissue to locate a lesion to position one end of a guide wire at the lesion to facilitate the introduction of a surgical instrument into the body and guidance of same directly to the lesion.

13 Claims, 9 Drawing Sheets

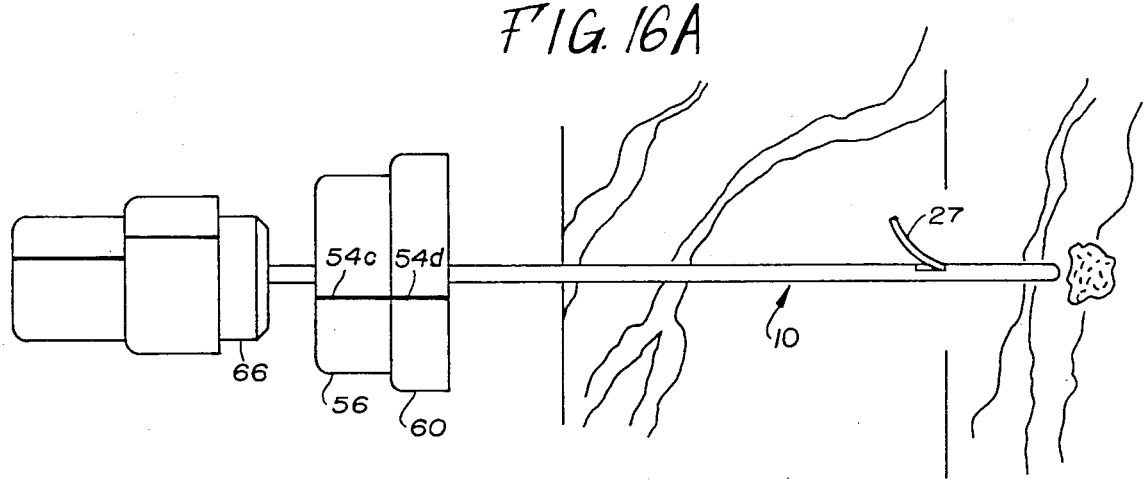
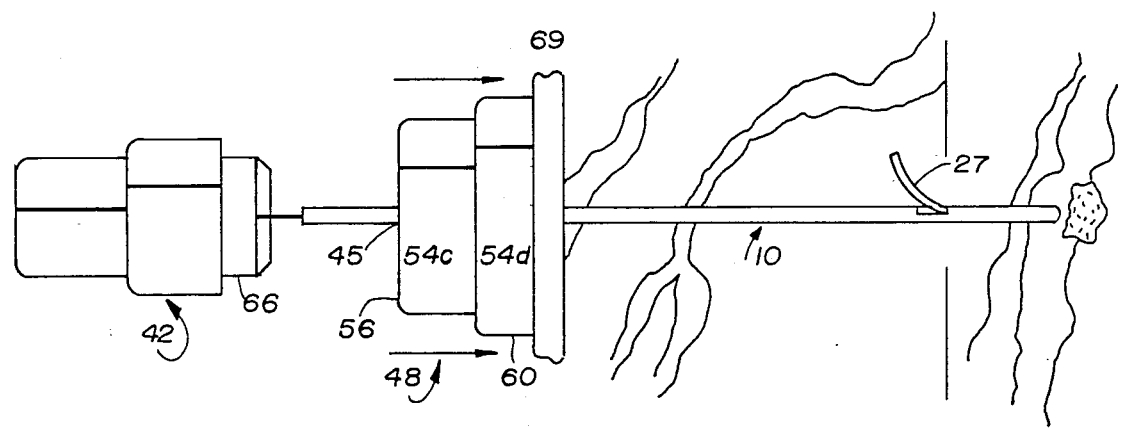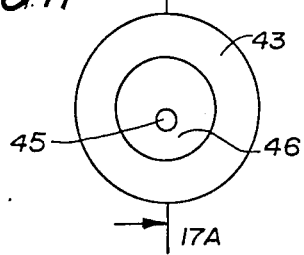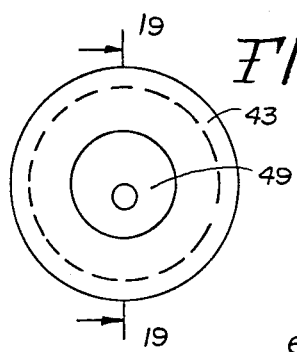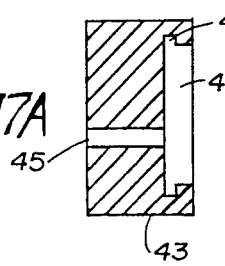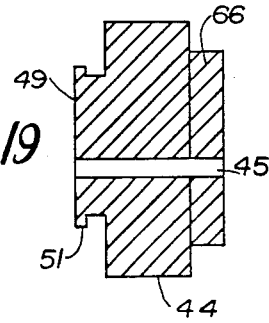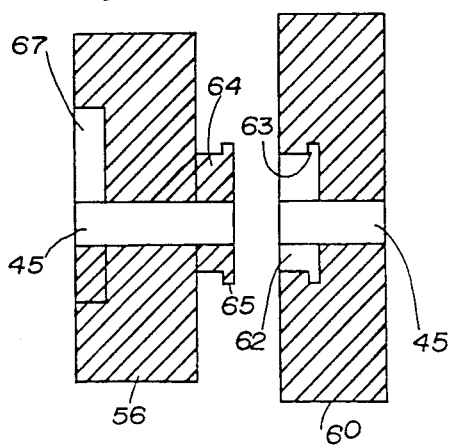

LOCALIZATION NEEDLE ASSEMBLY

BACKGROUND OF THE INVENTION

The present invention relates to a novel breast localization needle which may be readily inserted and anchored within the body tissue to identify to the surgeon the location of nonpalpable lesions.

During the past thirty years, there has not been a substantial increase in the rate of survival in the treatment of breast cancer using a surgical radiation therapy or chemotherapeutic treatment of the breast lesions, with the five year survival rate still being approximately 50%. However, if very small lesions, less than one centimeter in size, are detected early and appropriately surgically removed, the rate of survival is between 92 to 97%. The use of mammography, or X-ray examination, of the breast has been able to detect small lesions or tumors in asymptomatic females. Although, these lesions can be identified by X-ray examination, their surgical removal is often times difficult because they are small in size and they are difficult to precisely locate, especially in large breasts, and in the case where the lesions are located deep within the tissue mass.

To aid the surgeon in locating the nonpalpable lesions within the breast, Kopans has suggested and disclosed a technique (Radiology, March, 1980, Vol 128, p. 781) wherein a hypodermic needle is initially placed into the breast to locate the breast lesion. After the needle is positioned in the breast, the location is optimally confirmed by using two mammographic or X-ray positions. During these mammographic filmings the breast is compressed to confirm the positioning of the needle at or adjacent to the breast lesion. When the needle is properly placed, a stainless steel wire having a hairpin hooked-end portion is slid through the needle wherein the hooked hairpin-end portion exits from the needle to engage the body tissue to retain the needle adjacent to or at the breast lesion. Upon the exit of the hooked portion to engage the breast tissue, an additional set of mammograms is taken to verify the position of the hook, wire and needle with respect to the breast lesion. If the position is correct, the introducing needle is withdrawn over the wire and the wire is anchored to the tissue and the patient is taken to surgery. The wire permits the surgeon to know where the lesion lies within the breast tissue.

However, the Kopans' needle and wire-hook arrangement possesses several disadvantages because during mammographic filming of the breast lesion and location of the needle within the breast, the breast is compressed which can cause the needle to move or be displaced with respect to the breast lesion. Additionally, after the hairpin hook wire has been inserted through the needle and expanded to anchor the Kopan's needle/hook-wire apparatus in place, a second set of mammograms is required to verify the positioning of the needle within the breast tissue. If the position is incorrect, the hooked wire cannot be easily removed and forceful removal results in considerable damage to the tissue as well as the fact that the ultimate removal of the hook-wire from the breast causes undesirable tearing and damage to the breast tissue.

More recently, Homer has disclosed a needle/wire device and technique (Radiology, October, 1985, Vol. 157, pp. 259-260) which includes a curved-end wire which is made of tough pseudo-elastic alloy which possesses a memory. A needle containing a wire having a J-shaped hook on the end is inserted into the breast and advanced to identify the location of the breast lesion. The wire is then advanced inwardly such that the curved hooked end engages the body tissue to immobilize the needle during mammography imaging to insure that the needle is correctly positioned at or adjacent the breast lesion. Although such a curved J-shaped retractable wire within a stylus eliminates the need for multiple X-rays, the needle and hook device can be relatively easily displaced if traction or pressure is applied to the breast during transport of the patient or during surgery. Thus, actual migration of the hook-wire device in the breast tissue occurs during surgery and movement of the patient to surgery.

SUMMARY OF THE INVENTION

One object of the present invention is a novel breast localization needle which may be readily positioned and locked within the body tissue to precisely locate and pinpoint breast lesions for subsequent surgical removal or biopsy.

Another object of the present invention is a novel breast localization needle which includes one or more barbs which may be extended outwardly from the side walls of the needle to lock and anchor the needle within the body tissue to precisely locate breast lesions for subsequent surgical removal.

Still another object of the present invention is a novel breast localization needle which includes a helical screw needle tip on the distal end which may be readily positioned and locked within the body tissue to precisely locate breast lesions for subsequent surgical removal.

Still another object of the present invention is a novel breast localization needle which includes a flexible outer cannula portion which permits the positioning of the breast localization needle to locate deep breast lesions for subsequent surgical removal.

Still another object of the present invention is a pair of interlocking handle members which are engageable with respect to the outer cannella member and inner stylus member to assist in the insertion of the breast localization needle into the body tissue to locate breast lesions for subsequent surgical removal.

Still another object of the present invention is a remote incisional cannula accessory which is insertible over the breast localization needle to permit the surgeon to make a incision for removal of the breast lesion remote from the point of insertion of the breast localization needle into the body tissue.

Still a further object of the present invention is a novel nonpalpable lesion locator which may be inserted into a body tissue to pinpoint and locate the nonpalpable lesion.

A further object of the present invention is to provide a novel method for surgically removing lesions when the incision is made remote from the point of entry where the localization needle enters the body tissue.

With these and further objects of the present invention, the nature of which will become more apparent, the invention will be more fully understood by reference to the drawings, the accompanying detailed description and the appended claims.

DESCRIPTION OF THE DRAWINGS

FIGS. 16–16B are side views illustrating the locking members engaging the outer and inner cannula when the inner stylus has been retracted to expose the barb and anchor the needle within the body tissue;

FIG. 17 is a rear elevation view of the outer collar member of the proximal handle portion which engages the inner stylus member in accordance with the present invention;

FIG. 17A is a cross-sectional view taken along the lines 17A—17A of FIG. 17;

FIG. 18 is a front elevation view of the inner collar member of the proximal handle portion which is engageable with the inner needle stylus member of the localization needle in accordance with the present invention;

FIG. 19 is a cross-sectional view taken along the lines 19—19 of FIG. 18;

FIG. 20 is a cross-sectional view of the outer collar member of the distal handle portion which is engageable with the outer needle member of the localization needle in accordance with the present invention;

FIG. 21 is a cross-sectional view of the inner collar member of the distal handle portion which is engageable with the outer annular member of the localization needle in accordance with the present invention;

DETAILED DESCRIPTION

Figure 1:
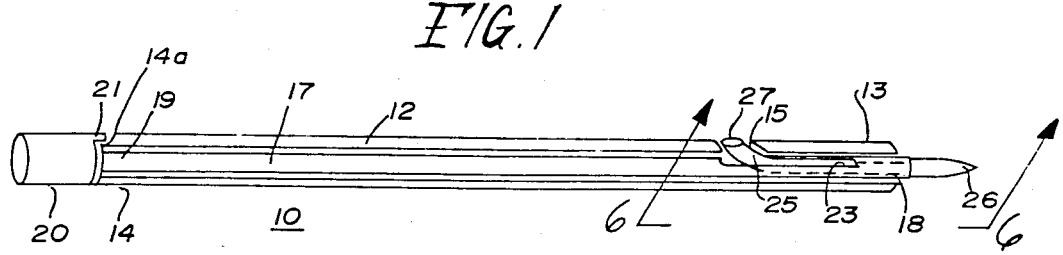
FIG. 1 is a side view of the breast localization needle in accordance with one embodiment of the present invention showing the displacement of the needle during insertion into the body tissue.
Figure 2:
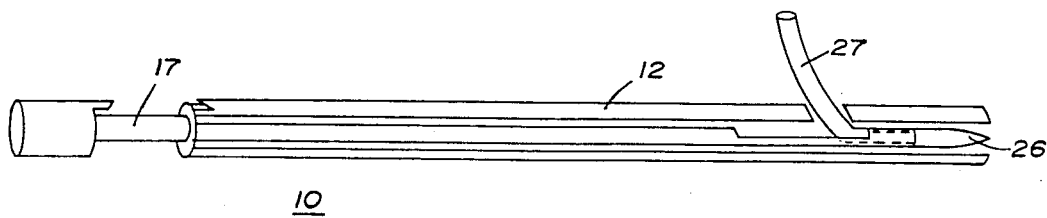
FIG. 2 is a side view of the embodiment shown in FIG. 1 showing the inner stylus retracted in the barb position within the body tissue to lock the breast localization needle in place.

Referring now to the drawings where like numerals have been used throughout the several views to designate the name or similar parts, in FIGS. 1 and 2 a breast localization needle assembly 10 is illustrated which includes an outer tubular needle or cannula member 12 having a distal end 13 and a proximal end 14. The needle or cannula member 12 may be comprised of a rigid material composed of either steel, polymer or a combination thereof and may be of a variable length as required. Although the needle assembly 10 has been specifically identified as a breast localization assembly, the needle assembly of the present invention has application in locating cancerous nonpalpable lesions within the human or animal body, be it a brain tumor, or any medical procedure which requires the pinpointing of a lesion, foreign body or normal structure within the body or organ of the body. The outer tubular needle cannula member 12 may include a single or multiple side holes or openings 15 in the sidewall which are of predetermined and variable distances from the distal end 13 of the cannula member 12. The needle assembly 10 further includes an inner stylus needle or annular member 17 which may be slidably advanced within the outer tubular cannula member 12 as desired. The inner cannula member 17 includes a distal end 18 and a proximal end 19, with a hub 20 mounted on the proximal end 19 of the inner cannula member 17. The hub includes a projection 21 thereon which cooperates with a recessed depression 14a of the proximal end 14 of the cannula member 12 to prevent rotation of the inner stylus or cannula member 17 with respect to the outer cannula member 12 during insertion of the needle assembly 10 into the body tissue.

Figure 6:
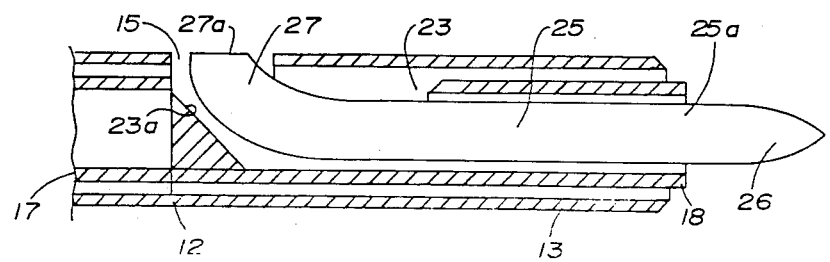
FIG. 6 is a sectional view taken along the lines 6—6 in FIG. 1.

As shown in FIGS. 1, 2 and 6, the inner stylus or cannula member 17 includes a cutaway portion or groove 23 therein adjacent to the distal end 18. The distal end 18 is, preferably, tubular and circular in shape and is adapted to receive a wire member 25 having a pointed end 26 which extends beyond the distal end 18. The forward end portion 25a of wire member 25 is secured to the distal end 18 by soldering, welding or by adhesion and the wire portion 25 includes a free end defining a proximal barb or hook member 27 which is adapted to be received in the cutaway or groove portion 23 of the inner stylus member 17. The rearward wall 23a of the groove 23 slopes upwardly towards the opening 15, defining a guide surface for the free, barb end 27 of the wire 25. The end 27a of the barb member is positioned within the opening 15 in the sidewall of the outer tubular needle member 12. As shown in FIGS. 1 and 6, the needle assembly 10 is so assembled that the pointed end 26 of the wire member 25 extends beyond the distal end 13 of the outer needle member 12 during insertion of the assembly into the tissue of the body, the position as shown in FIGS. 1 and 6.

When it is believed that the needle assembly 10 has been positioned adjacent to or at the lesion within the body or breast tissue, the hub 20 which is attached to the proximal end 19 of the inner cannula member 17 is pulled outwardly away from the proximal end 14 of the outer cannula member 12, which movement causes the barb member 27 to move outwardly through opening 15 in the sidewall of the outer cannula member 12, the position as shown in FIG. 2.

The needle assembly 10 is advanced into the target area of a human or animal body, either for simply making the location or removing any substance, fluid, tissue, tumor, blood or foreign body, be it the breast, liver, ductal structure, brain, lung or other organs where it is desirable to take a biopsy, a sample structure or to surgically remove an unwanted mass or lesion from the body. The desired position is obtained by advancing the needle assembly into the target area using the forward pressure on the hub 20 on the inner cannula member to advance the needle assembly into the target. After the needle has been properly positioned using either X-ray, ultrasound, or other filming means, the hub and inner cannula 17 is retracted and moved outwardly thereby deploying the barb member 27 through opening 15 in the sidewall of the outer cannula member to lock and firmly hold the needle in position within the body tissue. When the needle assembly 10 has been inserted into the breast, the movement of the barb member 27 into the body tissue anchors and firmly retains the needle assembly within the breast or body tissue. The location of the opening 15 in the outer cannula member 12 is predeterminedly from the distal end 13, as desired. That is the opening 15 may be located on the outer cannula at a position where it is desired that the needle assembly be anchored to the body tissue. Preferably this position is adjacent the distal end, but it could be located at any position intermediate the distal and proximal ends provided proper anchoring of the assembly occurs with respect to the body tissue.

Figure 3:
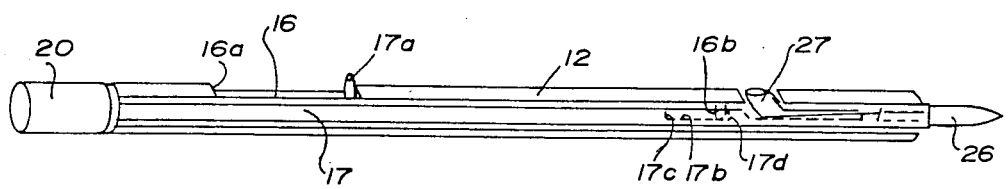
FIG. 3 is a side view showing a further embodiment of the breast localization needle wherein the inner stylus includes a projection thereon which cooperates with a slot in the outer needle section to facilitate insertion and retraction of the position barb within the body tissue.

If after deployment of the barb 27, it is determined by X-ray, ultrasound or filming means, that the needle assembly has not located a lesion, the barb 27 can be retracted by advancing the inner cannula 17 into the outer cannula 12. The needle assembly 10 can then be repositioned to locate the lesion, the inner cannula 17 being moved outwardly of the outer cannula to again deploy the barb when the lesion is located. Additionally, the hub projection 21 during the insertion mode is adapted to rest and be received by the recessed depression 14a in the outer cannula member. This indexes the inner stylus cannula member with respect to the outer cannula member 12 and prevents rotation of the inner cannula member 17 with respect to the outer cannula 12 which could cause dislocation of the barb member 27 from the aperture 15 in the outer cannula member 12. As is well known in the art, the length of the outer cannula member 12 can vary depending upon the depth of the lesion that is to be localized and identified for subsequent surgical operation. Additionally, as shown in FIG. 3, the outer cannula member may have an elongated slot 16 positioned therein which cooperates with a projection 17a on the inner cannula member 17. Thus, the projection 17a, as shown in FIG. 3, is in its forward position within slot 16 during insertion of the assembly into the body tissue. The slot 16 confines the movement of the projection 17a on the inner cannula member 17 such that when the hub 20 is retracted outwardly and the barb member is exposed, as shown in FIG. 2, the projection will engage a stop surface 16a defined by the outer proximal end of the elongated slot 16. Thus, the slot 16 and the projection 17a on the inner cannula member 17 cooperate to confine the forward and rearward travel of the inner cannula member 17 to maintain the barb member 27 within the opening 15 in the sidewall of the needle assembly 10 as desired. Alternatively, the outer cannula 17 may have a projection 16b shown by dashed line in FIG. 3, depending from the inner surface thereof into a slot or channel 17b having end walls 17c and 17d, shown by dashed lines in FIG. 3, and cooperating therewith to limit travel of the inner needle 17 in movement between its extended portion, where projection 16b engages end 17d, and its retracted position where projection 16b engages end 17c.

Figure 4:
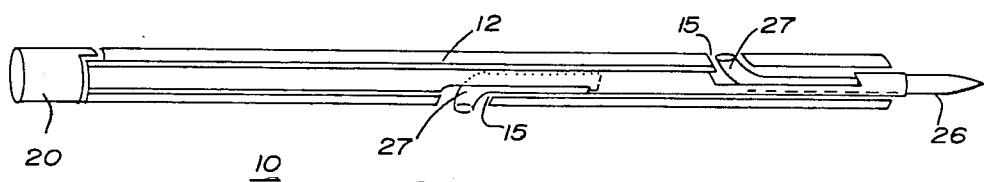
FIG. 4 is a further embodiment of the breast localization needle having more than one barb cooperating with openings in the side wall of the needle during insertion of the needle into the body tissue.
Figure 5:
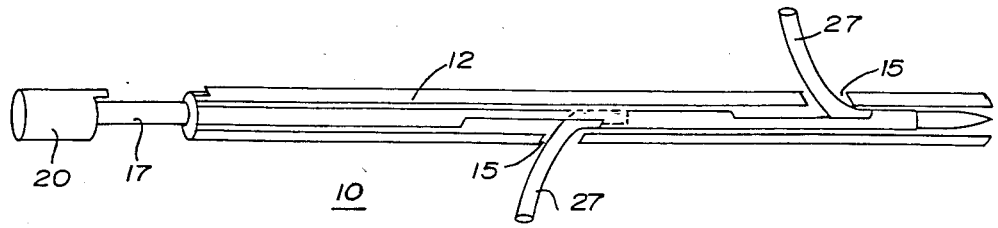
FIG. 5 is a side elevation view of the embodiment shown in FIG. 4 showing the barbs exposed and locking the breast localization needle in place within the body tissue.

FIGS. 4 and 5 illustrate a further embodiment of the breast localization needle assembly 10 which comprises a plurality of openings 15 in the sidewall of the outer needle or cannula member 12. As illustrated in these drawings, the inner cannula member 17 has more than one barb member 27 mounted to the inner cannula member 17 each of which cooperates and moves outwardly through an associated opening 15 in the sidewall in the needle assembly 10. The operation of the needle assembly 10 is identical with the operation as described for the assembly as shown in FIGS. 1 through 3.

Figure 6A:
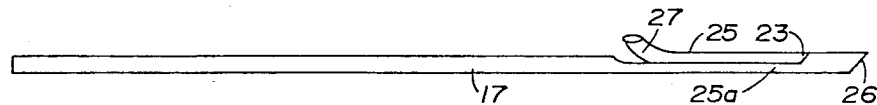
FIG. 6A is a side elevational view of a further embodiment of an inner stylus for the breast localization needle in accordance with the present invention.
Figure 6B:
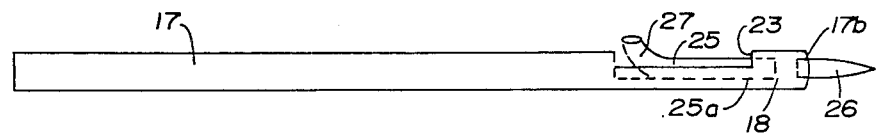
FIG. 6B is a side elevational view of a further embodiment of an inner stylus for the breast localization needle in accordance with the present invention.

FIGS. 6A and 6B illustrate further embodiments of the inner stylus 17 of the needle assembly 10. In FIG. 6A, a groove or channel 23 is formed in the upper surface of a conventional needle 17 near its distal end 18, rearward of the top of the needle 17. A short wire segment or member 25 is located in the groove 23 with its forward end 25a secured therein and its other end free, defining rearwardly projecting barb member 27.

In FIG. 6B, the distal end 18 of the inner stylus 17 has a groove or channel 23 formed therein which receives a wire segment 25. The forward end 25a of the wire segment is secured to the stylus 17 within the groove 23 and its other end being free defining rearwardly projecting barb member 27. A pointed tip member 26 is secured to the forward end of the stylus 17 in a recess 17b formed in the forward end of the stylus.

Figure 7:
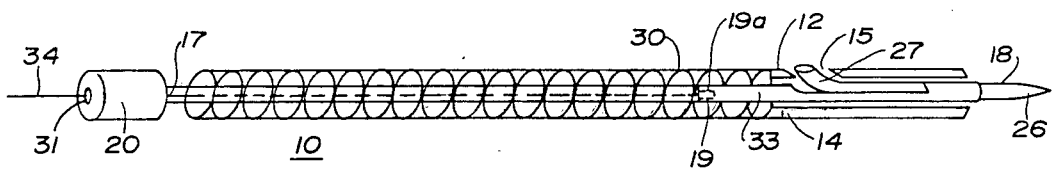
FIG. 7 is a side elevational view of a further embodiment of a breast localization needle in accordance with the present invention.
Figure 8:
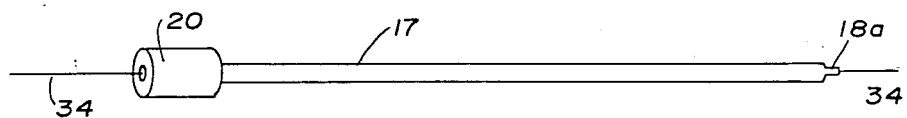
FIG. 8 is a side view of the inner stylus the used in inserting the localization needle of the embodiment of the present invention as shown in FIG. 7.
Figure 9:
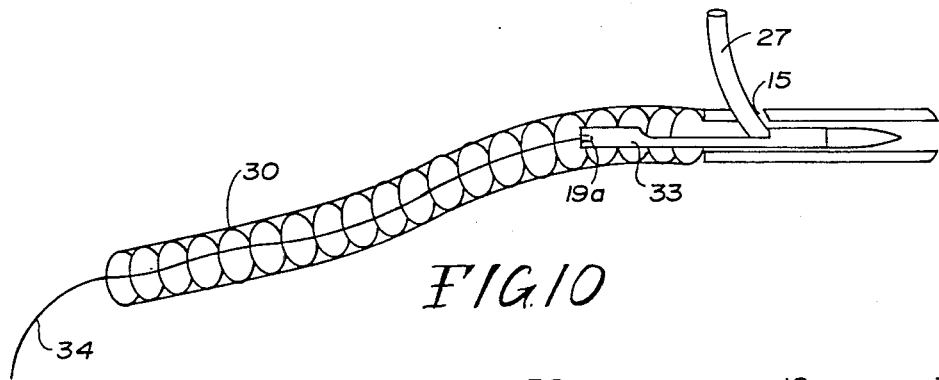
FIG. 9 is a side view of the embodiment of the present invention as shown in FIG. 7 with the inner stylus removed from the localization needle.

FIGS. 7-9 illustrate a further embodiment of the present invention wherein the needle assembly 10 is comprised of a shortened outer tubular needle or cannula member 12 which is fixedly attached, preferably to a tubular spring helix 30 or any flexible tube at the proximal end 14 of the outer cannula member 12. The tubular helix 30 is impregnated or coated with a polymeric material, in a manner similar to the procedure described in U.S. Pat. No. 4,004,765. Thus, the spring helix 30 is joined at the proximal end 14 of the outer cannula member 12 with the resultant spring helix cannula portion thereof being flexible to prevent the possibility of inadvertent displacement of the needle assembly 10 deeper into a breast, lung or other vital organ with locating a lesion therein because of compression of the target during film imaging. The needle assembly 10 includes an elongated inner stylus or cannula member 17 having a hub 20 positioned on the end thereof with the inner cannula member 17 being tubular in shape and defining a passageway 31 therethrough. The inner cannula member 17 is further comprised of a forward portion 33 having a distal end 18 thereon with a tapered pointed end 26 extending forwardly therefrom. Rearwardly of the distal end 18 is a barb member 27 which is adapted to be received within the forward portion which cooperates with an opening 15 in the outer cannula member 12 in much the same manner as described above with respect to figures 1 through 5. The forward portion of the inner cannula member 17 is attached to a flexible wire or monofilament welded or bonded to the end of the forward portion of the inner cannula member 17. The wire or monofilament 34 extends through passageway 31 in the tubular inner cannula member 17 as shown in FIG. 7. The inner stylus or cannula member 17 has a distal end 18a (FIG. 8) which matingly cooperates and engages the recessed annular shoulder 19a on the proximal end 19 of the forward portion 33. Such a cooperation assures registration of the cannula member 17 and the forward portion 33 during insertion into the body tissue when cannula member 17 is utilized to stiffen the needle assembly 10, as shown in FIG. 7.

When the needle assembly is advanced as a single unit into the target area, once the target has been entered, the wire or monofilament 34 is retracted deploying the barb member 27 through opening 15 in the outer cannula member 12, as shown in FIG. 9. Once the target and the barb has been deployed, the inner cannula member 17 is removed from within the outer cannula member 12 and spring helix 30, thus creating a flexible localization needle assembly 10, as shown in FIG. 9. If by chance the needle assembly 10 requires relocation, the inner cannula member 17 is advanced over the wire or monofilament 34 to engage distal end 18a with the recessed annular shoulder to stiffen the needle assembly and to thereby retract the barb member 27 and reposition the needle as desired.

Figure 10:
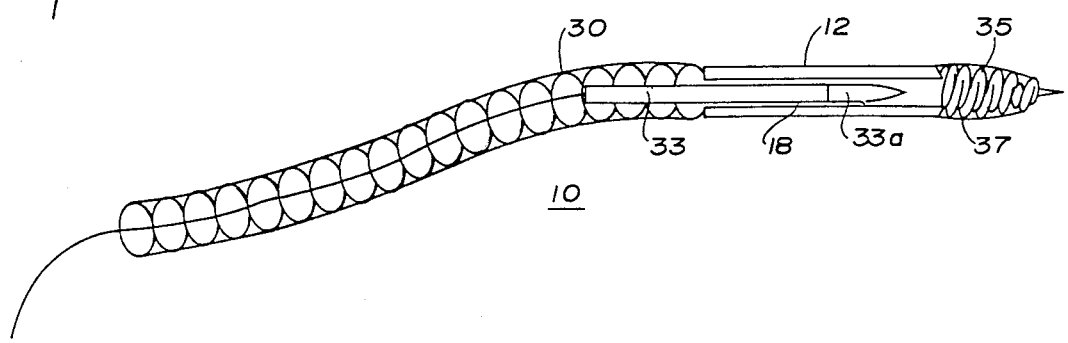
FIG. 10 is a further embodiment of the present invention showing a needle screw mounted to the end of the needle for anchoring and drawing the needle within the body tissue to locate a lesion therein.

FIG. 10 illustrates a further modification of the needle assembly 10 which is comprised of an outer tubular cannula member 12 attached to a spring helix 30 or flexible tube which has been coated by a procedure disclosed by U.S. Pat. No. 4,004,765. However, the outer cannula member 12 does not have an opening 15 in the side thereof and the forward portion 33 of the inner cannula member includes only a sharp projection 33a extending beyond the distal end 18 of the forward portion of the inner cannula member 17. Attached to the distal end 13 of the outer cannula member 12 is a helical screw needle 35 which is tapered to a fine point which provides a screw-type configuration which will lock the needle assembly 10 into the body tissue or any other target by clockwise rotation of the assembly. After X-ray or other filming confirms the correct position of the needle assembly 10, the inner stylus or cannula member 17 is withdrawn (not shown in FIG. 10) and the helical screw member 35 performs the function of anchoring the needle assembly within the target area.

Although it is not shown in FIG. 10, it is within the scope of the present invention that the mounting of the helical screw needle 35 upon the distal end 13 of the outer tubular cannula member 12 can be used with the inner stylus cannula member 17, as shown in FIG. 8, without the use of a wire member or pointed end attached to the inner cannula member 17 and the proximal end thereof. In such an embodiment it is proposed that a very thin polymer catheter coating or cover 37 may be used to cover the outside surface of the helical screw assembly 35 to facilitate insertion of the needle assembly into the body tissue. After insertion of such an assembly into the body tissue, rotation of the needle assembly 10 facilitates engagement of the helical screw needle with the body tissue to properly anchor the needle assembly in the body tissue.

Figure 11:
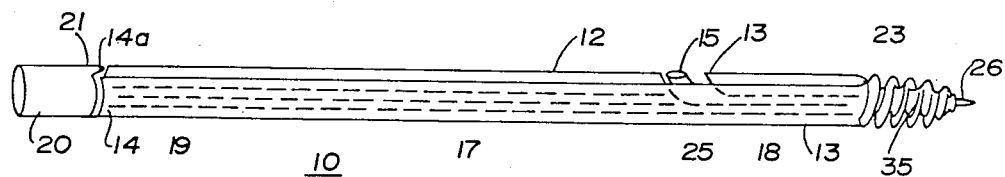
FIG. 11 is a side view of a further embodiment of a breast localization needle wherein the needle possesses a screw thread on the end thereof for drawing the needle into the body tissue and for anchoring the needle within the tissue.
Figure 12:
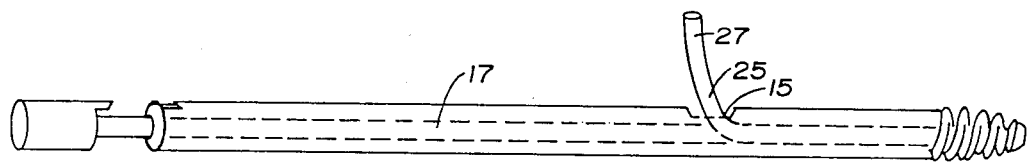
FIG. 12 is a side view of the embodiment shown in FIG. 11 showing the inner stylus retracted with the barb extending outwardly through the side wall thereof when the inner stylus is retracted after insertion of the needle into the body tissue.

FIGS. 11 and 12 further illustrate another embodiment of the present invention which is similar to the embodiment disclosed in FIGS. 1 and 2 but wherein a helical screw needle member 35 is securely fastened to the distal end 13 of the outer tubular cannula member 12. In this embodiment of the localization needle assembly 10, the outer tubular cannula member 12 is comprised of a rigid material composed of either steel, polymer, or a combination thereof and which may be of variable length, as required. The outer tubular cannula member 12 may include single or multiple side holes or openings 15 which are predeterminely located from the distal end 13 of the outer cannula member 12. The assembly 10 includes also an inner cannula member 17 which is slidably advanced within the outer cannula member 12. The inner cannula member 17 includes a distal end 18 and a proximal end 19 with a hub 20 mounted on the proximal end 19 of the inner cannula member 17. The hub includes a projection 21 which cooperates with a recessed depression 14a in the proximal end 14 of the outer cannula member 12 to prevent rotation of the inner cannula member 17 with respect to the outer cannula member 12 during insertion of the needle assembly into the body tissue. In the same manner as shown in FIGS. 1, 2 and 6, the inner cannula member 17 includes a cutaway portion or groove 23 which is adapted to receive a wire member 25 having a pointed end 26 which extends upon the distal end 18 of the inner cannula member 17. The wire member 25 includes a hook portion 27 which is adapted to be received in the groove of the inner stylus member and is positioned within the opening 15 of the sidewall of the outer needle member 12 when the assembly is inserted within the body. As shown in FIG. 11, the pointed end 26 of the wire member 25 extends beyond the distal end 13 of the helical screw needle 35 which is attached top the distal end 13 of the outer cannula member 12 and is tapered to a fine point which permits a screw-type configuration which aids in locking the needle assembly 10 to the body tissue or other target as previously described. In FIG. 12, the inner member 17 has been retracted thereby positioning the barb member 27 into the body tissue adjacent to the assembly 10.

Figure 13:
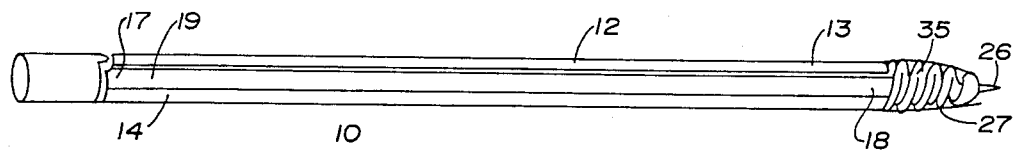
FIG. 13 is a further embodiment of a lesion localization needle with the outer needle portion having a screw thread mounted to the distal end of the needle to facilitate insertion and anchoring of the needle within the body tissue.

FIG. 13 illustrates a localization needle assembly 10 which does not include the structure wherein the inner stylus or cannula member 12 includes a cutaway portion with a wire member 25 mounted therein which includes a barb portion which extends through an opening in the sidewall of the outer cannula member 12. Instead, the embodiment of FIG. 13 includes a tubular outer cannula member 12 having a distal end 13 and a proximal end 14. Mounted to the distal end 13 is a helical screw needle 35 and the outer cannula member 13 is adapted to slidably receive an inner cannula member 17. The inner cannula member 17 may have a distal end portion 18 which includes either a pointed end 26 or it can itself be a very fine needle having a point thereon. Thus, in the fully inserted position, as shown in FIG. 13, the needle assembly 10 is screwed or turned into the body tissue to locate the lesion for subsequent surgical removal. Again, the helical screw needle may include a polymer catheter cover 37, as previously shown in FIG. 10, to facilitate insertion of the needle assembly 10 into the body tissue.

Figure 14:
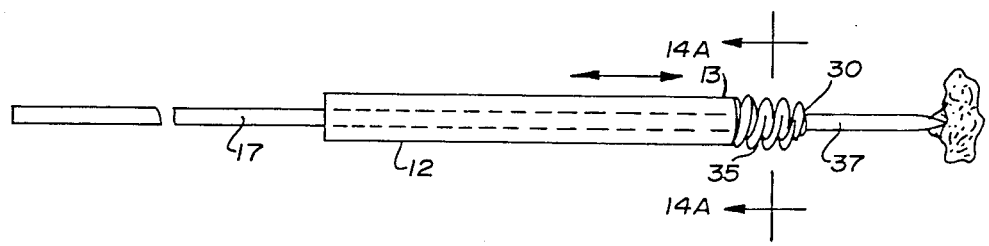
FIG. 14 is a side view of a further embodiment of the present invention illustrating the placement of a sheath cannula having a helical screw distal end being directed to a lesion over a fine guide needle used to locate the lesion.
Figure 14A:
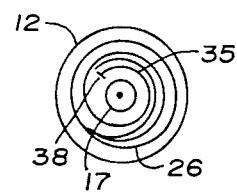
FIG. 14A is a sectional view taken along lines 14A—14A of FIG. 14.
Figure 14B:
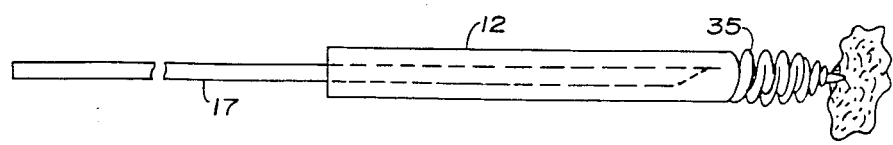
FIG. 14B is a view similar to FIG. 14 illustrating the removal of the fine guide needle from the body tissue and the anchoring of the sheath cannula of the nonpalpable lesion.

A further embodiment of the localization needle assembly 10 is shown in FIGS. 14 and 14A wherein the inner cannula member 17 is a very small diameter guide needle of approximately 22 gauge, which extends the length thereof. The guide needle is used to probe the particular body tissue to identify the lesion or to probe the particular organ into which the needle assembly is to be inserted. After the inner cannula member 17 locates the particular lesion or area of the organ to be localized, an outer cannula member 12, of approximately 18–20 gauge, is slidably advanced over the inner cannula member or needle 17. The outer cannula member includes at its distal end 13 a helical screw needle 35 thereon, which has an opening 38 in the end so that it may be encircled and advanced over the inner cannula or needle member 17. When the outer cannula member 12 is positioned adjacent the target area, with rotation of the outer cannula member 12, cannula member 12 helical screw needle is advanced into the organ or breast tissue area, anchoring the needle assembly therein. Such a needle assembly is very advantageous when the lesion is very deep within the body or the organ is difficult to penetrate and hold and retain the needle assembly within the body for subsequent surgical removal or biopsy. When the helical screw needle anchors the needle assembly to organ or breast tissue area, the guide needle is withdrawn, as shown in FIG. 14B. This design works particularly well for gaining access to difficult scarred target areas.

Figure 15:
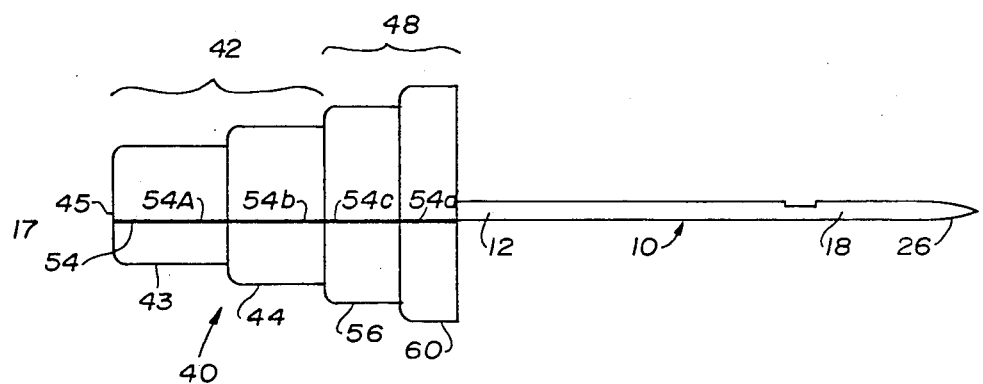
FIGS. 15–15A are side views showing the positioning of handle and locking members about the outer and inner stylus members of the breast localization needle in accordance with the present invention.
Figure 15A:
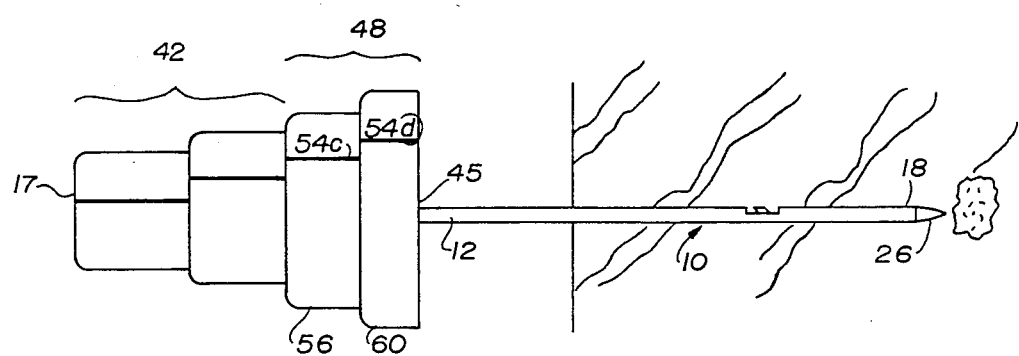

FIGS. 15–15A illustrate a handle and locking means which may be utilized in conjunction with the localization needle assembly 10 to position the needle assembly within the body tissue to pinpoint the lesion or body organ to be localized. The handle and locking means 40 is comprised of an outer proximal handle portion 42 and a distal handle portion 48. The proximal handle portion 42 is comprised of an outer collar member 43 and an inner collar member 44. The distal handle portion 48 is composed of an outer collar member 56 and an inner collar member 60. An alignment marking 54 for the handle and locking means 40 includes segments 54a–54d for the four collar members 43, 44, 56 and 60, respectively. Each of the collar members 43 and 44 of the proximal handle portion 42 has an off-center bore 45 extending therethrough. The dimension of the off-center bore 45 in the outer and inner collar members 43 and 44 is sized to be slidably engageable with the outer surface of the inner stylus or cannula member 17 of the various embodiments of the present invention. The outer collar member 43, as shown in FIGS. 17 and 17A has a female recess 46 and cooperating flange 47 which is adapted to receive a complementary projection 49 on the inner collar member 44 which has an annular flange 51 partially therearound to enable the outer and inner collar members 43 and 44 to be matingly engaged together when the outer alignment markings 54a and 54b on the outer surfaces of the collar members 43 and 44 are aligned, as shown in FIG. 15, the proximal handle portion 42 may be slidably engaged onto the inner cannula member 17. Rotation of collar members 43 and 44 of the proximal handle portion 42 in opposite directions causes the off-center bore 45 within each of these collar members to lock to and firmly retain the inner cannula member 17 in a fixed position.

Similarly, distal handle portion 48 of the handle and locking means 40 includes an outer collar member 56 and an inner collar member 60 which may be locked together to engage the outer cannula member 12 in the same manner that the collar members 43 and 44 of the proximal handle portion 42 are engageable with and lock to the inner cannula member 17. As shown in FIGS. 16–16B, and FIGS. 20 and 21, the outer collar member 56 and the inner collar member 60 each include an off-center bore 45 therethrough with the inner collar member 60 including a recess 62 therein and an annular flange 63 which are adapted to receive a projection 64 and annular flange 65 on the outer collar member 56. When the collar members 56 and 60 are matingly engaged together, the off-center bore 45, which is larger than bore 45 slidably receives the outer cannula member 12 therein, when aligned to the position as shown in FIG. 15 with alignment markings 54c and 54d aligned. When the collar members 56 and 60 are rotated in opposite directions until the alignment markings 54c and 54d are as shown in FIG. 15A, the off-center bore 45 extending through the assembled collar members 56 and 60 cause the distal handle portion 48 to firmly lock to the outer cannula member 12, the position as shown in FIG. 15A. It is within the scope of the present invention that either the distal handle portion 48 or the proximal handle portion may be used alone to engage and lock to an elongated tube, wire or a cannula member to permit the tube, wire or cannula member to be maneuvered by the user as desired.

For the purpose of locking the two handle portions 42 and 48 together, the inner collar member 44 of the proximal handle portion 42 has an annular projection 66 which is recessed in friction fit relation in a complementary shaped recess 67 formed in the outer collar member 56 of the distal handle portion 48 when the two handle portions are assembled together on the needle assembly 10 as shown in FIGS. 15 and 15A. When the alignment markings 54 are all aligned as shown in FIG. 15, the two handle portions 42 and 48 are movable as a unit along the length of the needle assembly 10. When the collar members of the two handle portions 42 and 48 are adjusted to the portions shown in FIG. 15A, the proximal handle portion 42 is locked to the inner stylus 17, the distal handle portion 48 is locked to the outer needle and the two handle portions are frictionally held together.

Figure 16:
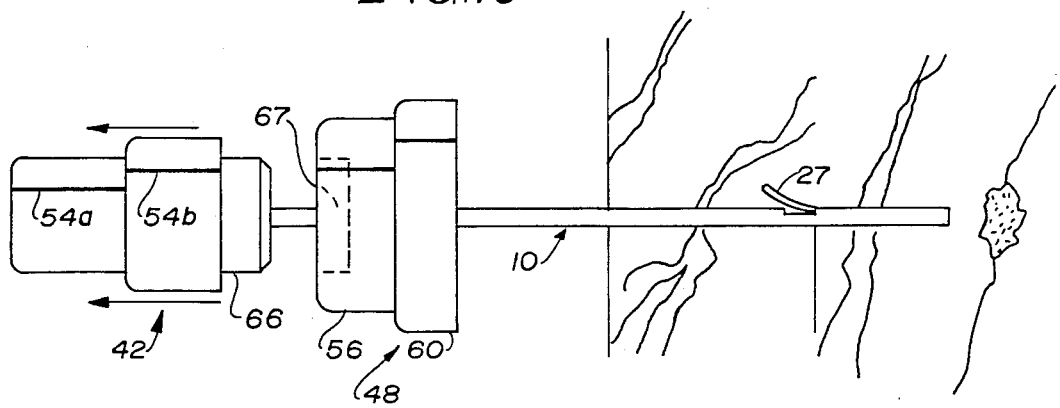
Figure 22:
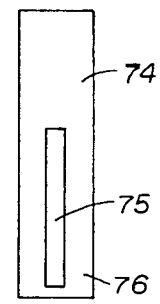
FIG. 22 is a side view of a cylindrical hollow cannula which is positioned about the breast localization needle for guide and insertion therearound into the body which permits the surgeon to position a guide wire at the location of a lesion in the body tissue.
Figure 23:
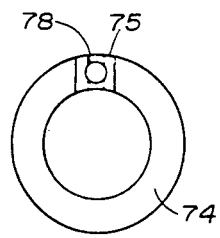
FIG. 23 is a cross-sectional view taken along lines 23—23 of FIG. 22.

When the entire handle and locking means 40 is locked together onto the localization needle assembly 11, as shown in FIG. 15A the pointed end 26 of the distal end 18 of the inner cannula member 17 is locked in the outward position and the needle assembly is inserted into the body or breast tissue in an effort to pinpoint and locate the lesion, as shown in FIG. 15A. When the lesion has been pinpointed, the proximal handle portion 42, which is locked to the inner cannula member 17 is retracted as shown in FIG. 16. As the proximal handle portion 48, the barb member 27 is extended into the breast or body tissue to anchor the needle assembly 10 within the body tissue. If a mammogram, or other filming, indicates that the needle is not correctly pinpointing or locating the lesion, then the barb may be retracted by moving the proximal handle portion 42 back towards the distal handle portion 48 to retract the barb and extend the pointed end 26 of the distal end 18 and the needle can be repositioned. After correct positioning of the needle, and after the barb member has been extended into the body or breast tissue to anchor the assembly, the distal handle portion 48 is moved to engage the body at the point of entry of the needle assembly. First, the collar members 56 and 60 are rotated to align the outer alignment markings 54c and 54d, the position as shown in FIG. 16B. Thereafter, a donut-shaped resilient sponge washer 69 is positioned about the needle assembly 10 between the surface of the skin and the distal handle portion 48 and the distal handle portion 48 is actually moved inwardly to slightly compress the resilient or foam cushion 69 to stabilize the needle assembly locked within the body tissue of the patient and the patient is transported from radiology to surgery for removal of the lesion. The resilient foam cushion 69 prevents and cushions the relative movement between the body of the patient and the locked position of the needle assembly to prevent dislocation of the needle assembly during transport of the patient to lock the distal handle portion 48 to the needle assembly 10, the collar members 56 and 60 are rotated in opposite directions to the position as shown in FIG. 16B.

After the patient arrives in surgery, the outer alignment marking 54 on the proximal handle portion 42 are aligned and the proximal handle portion 42 may be slidably removed from the inner cannula member 17. In the same manner the distal handle portion 48 as the outer alignment markings 54 on the outer collar member 43 and inner collar member 44 align and the distal handle portion 48 is slidably removed from the outer cannula member 12. The surgical sterilization occurs and the surgeon holds the needle and cuts down and removes the lesion that has been localized and pinpointed by the needle assembly in accordance with the present invention.

Figure 24:
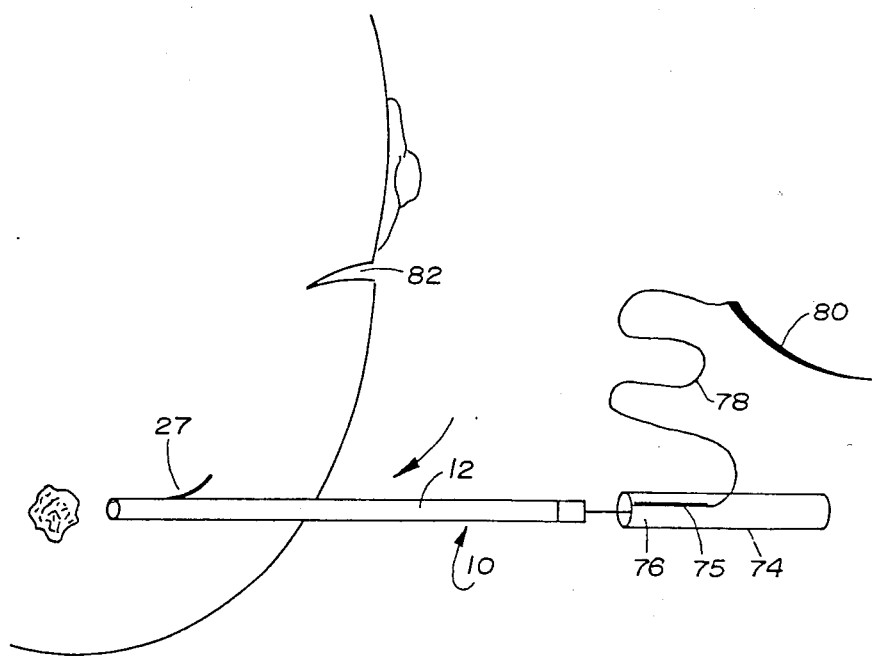
FIG. 24 is a perspective view showing the insertion of the breast localization needle within the body tissue and the partial insertion of the hollow outer cannula as shown in FIG. 22 thereabout.
Figure 25:
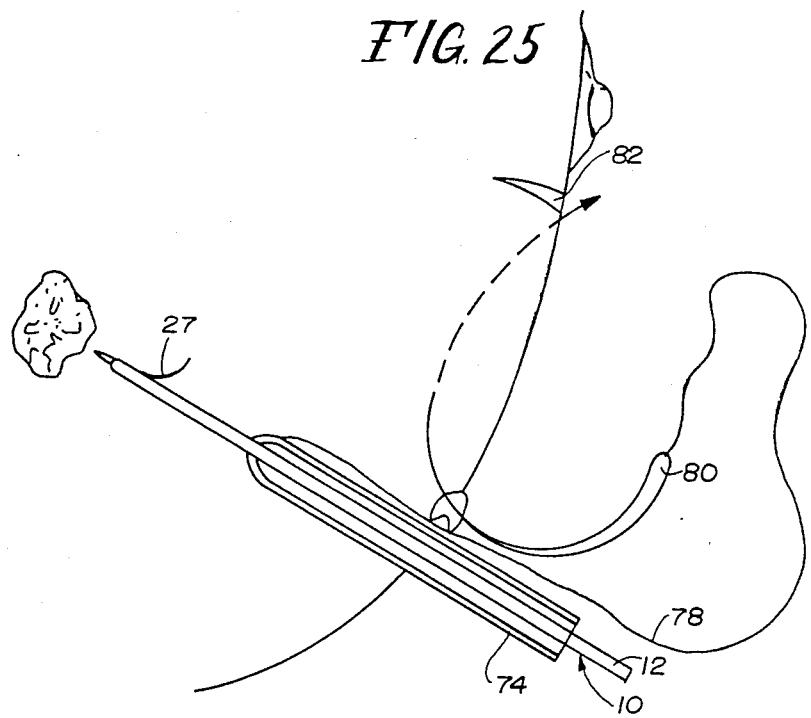
FIG. 25 is a perspective view illustrating the full insertion of the outer hollow cannula about the localization needle and the insertion of a guide needle portion of the hollow outer cannula through the skin adjacent to the localization needle entry point with the guide needle being laterally displaced along the interior of the body tissue to exit a point remote from the entry point of the localization needle.
Figure 26:
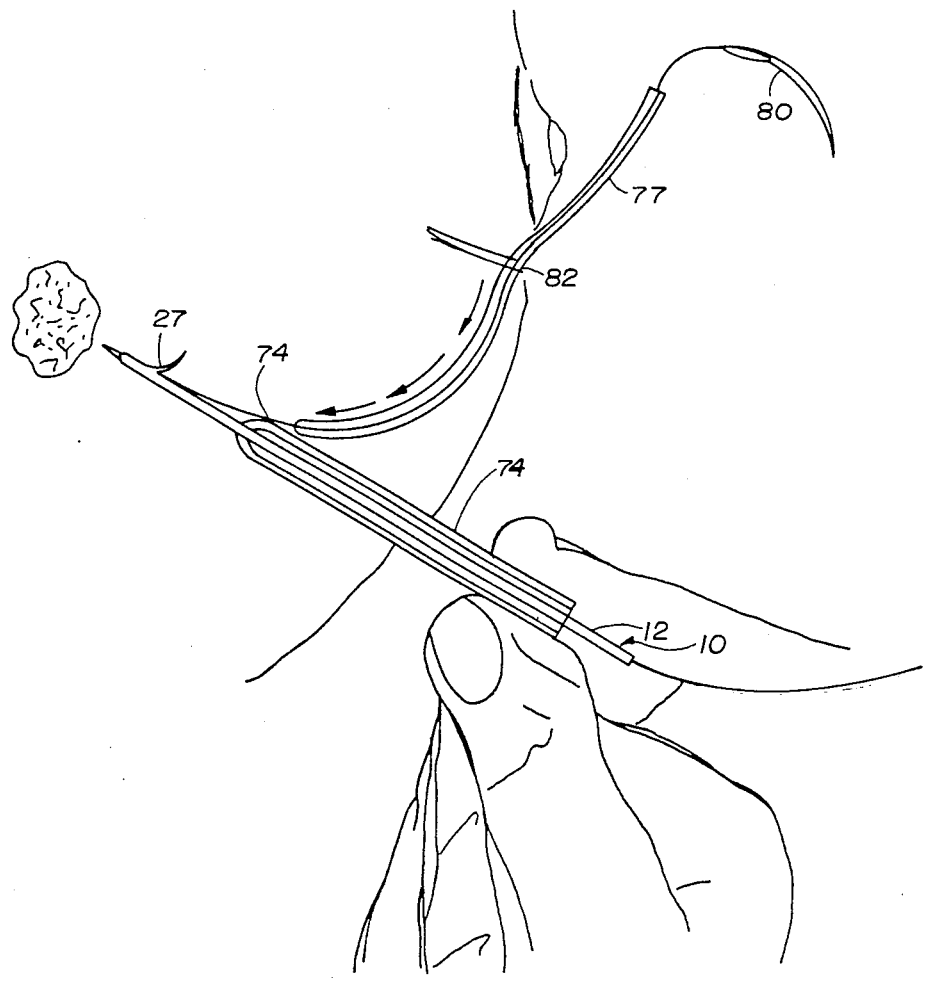
FIG. 26 is a perspective view showing the advancement of a tube member over the guide wire to identify a surgical path for the surgeon to surgically remove the lesion within the body tissue.
Figure 27:
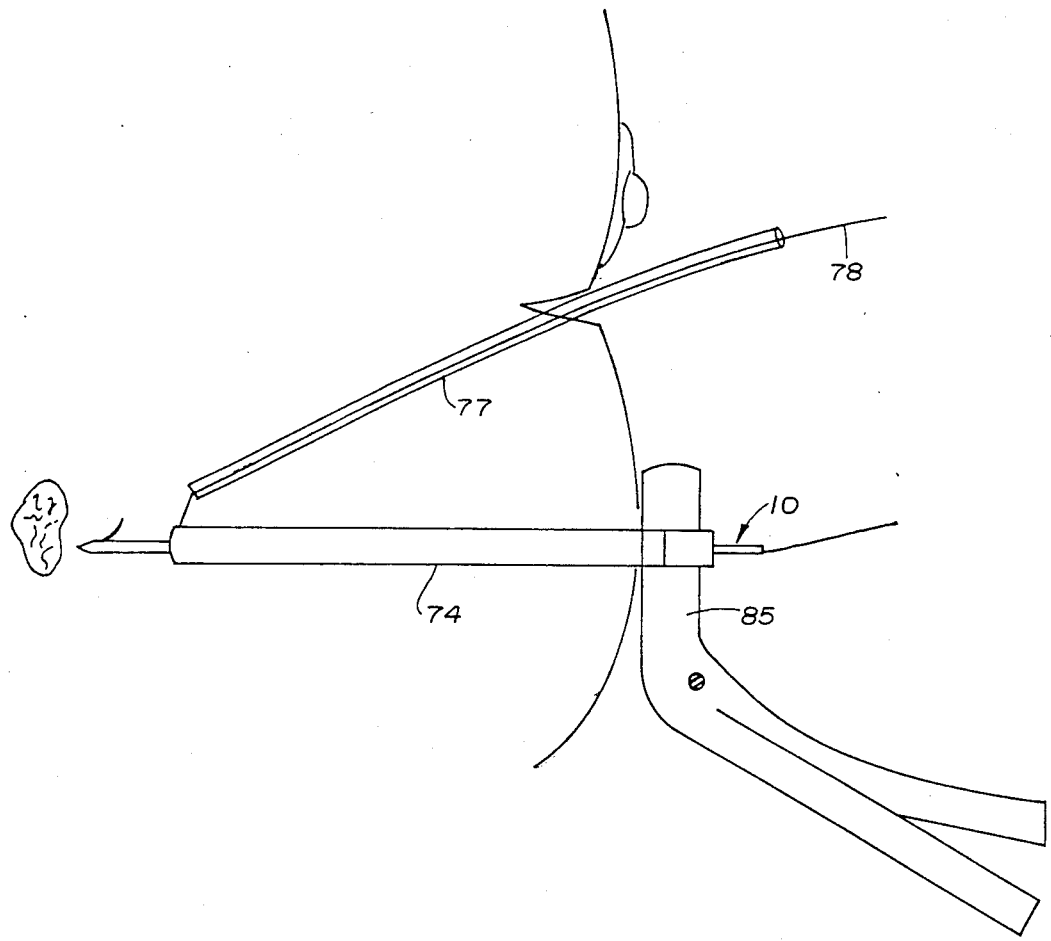
FIG. 27 illustrates a clamping device engageable with the localization needle to retain the same within the body tissue during surgery.
Figure 28:
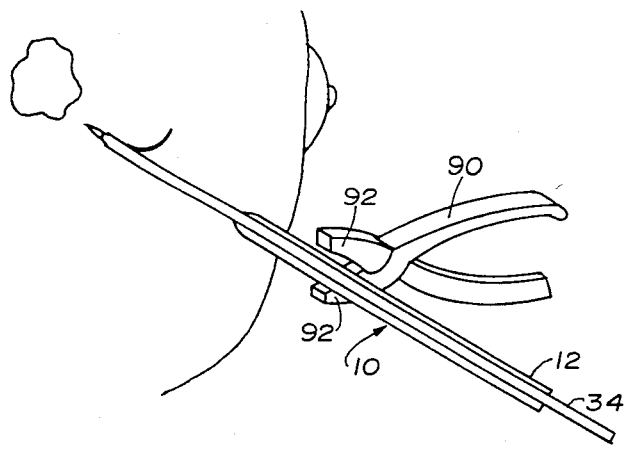
FIGS. 28-31 illustrate a cutting and crimping device in accordance with the present invention which is engageable with the breast localization needle, and illustrate the crimping and compressing components of the breast localization needle together to permit the use of long localization needles and shortening the same prior to transport of the patient from the radiology area to the operating room.

FIGS. 22–26 further illustrate another accessory for use with the breast localization needle assembly 10 which permits the surgeon to make an incision in the body of the patient at a point a distance from the position where the needle placement has penetrated the body of the patient so as not to leave a permanent scar. The accessory is used for locating a guide wire at a target area, to allow the surgeon to position a surgical instrument, such as an arthroscopic tube or instrument, etc., which requires a relatively large incision in the body, directly at the target area. The accessory includes a tubular cylindrical hollow cannula 74 which is sized and adapted to be slidably engaged over the outer cannula member 12. A surgical needle 80 is attached to the cannula 74 by a wire or monofilament material 78. For example, if the outer cannula member 12 is 20 gauge, the cylindrical hollow cannula 74 can be 18 gauge. The cylindrical hollow cannula has an axial groove 75 extending along its length that terminates at the distal end 76 of the hollow cannula 74. Preferably, the hollow cannula has a smooth tapered end 76 to provide a snug fit against the outer diameter of the outer cannula member 12. The tapered distal end 76 enables the user to slide the hollow cannula 74 along the outer cannula member 12 through the body structure or tissue to the target with minimal damage. The axial groove may be cut entirely through the wall length of the hollow cannula 74 or may be substantially through the thickness wall of the floor anchored at the distal end 76 within the axial groove is the wire or monofilament material 78 which extends upwardly along the hollow cannula floor within the axial groove 75 then axially along the outside of the hollow cannula 74. Attached to the end of the wire 78 surgical needle 80 as shown in FIGS. 24 and 25. When the needle assembly 10 has been inserted and positioned within the breast, and the barb member 27 has been exposed to anchor the needle assembly within the breast, the cylindrical hollow cannula 74 is inserted over the outer cannula member 12 and slidably advanced therealong into the breast tissue, the position as shown in FIG. 25. At the same time, the guide wire material 78 positioned alongside the hollow cannula 74 is advanced into the breast tissue. The free end of the guide wire 78, to which the needle 80 is attached, extends outwardly from the surface of the breast. As shown in FIG. 25, after the hollow cannula 74 is advanced to a variable distance over the localizing needle assembly 10 and particularly to the target area, the surgical needle 80 is advanced into the skin exactly at the point where the monofilament or wire 78 exits the skin adjacent the hollow cannula 74. The needle 80 is then advanced subcutaneously through the tissue to a remote point 82, such as just beneath the nipple, as shown in FIG. 25. After the needle has been pulled out of the remote area 82 an anthroscopic tube 77 (metallic or polymer) is advanced over the wire 78 which follows the wire to the point of attachment at the distal end 76 of the hollow cannula 74. Thereafter, the arthroscopic tube 77 may advance along the outer surface of the outer cannula member 12 to surgically biopsy the lesion or surgically remove the same. If desired, during this surgical procedure, the needle assembly 10 may be stabilized with either a clamp 89 or manually, as shown in FIG. 27.

Figure 29:
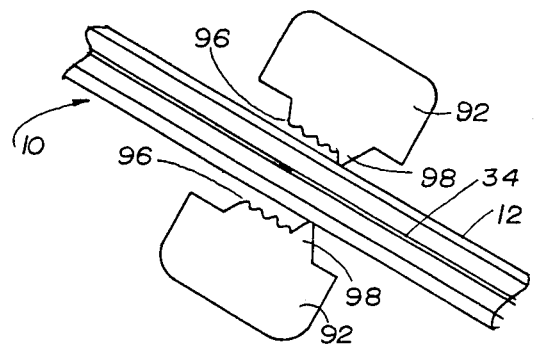
Figure 30:
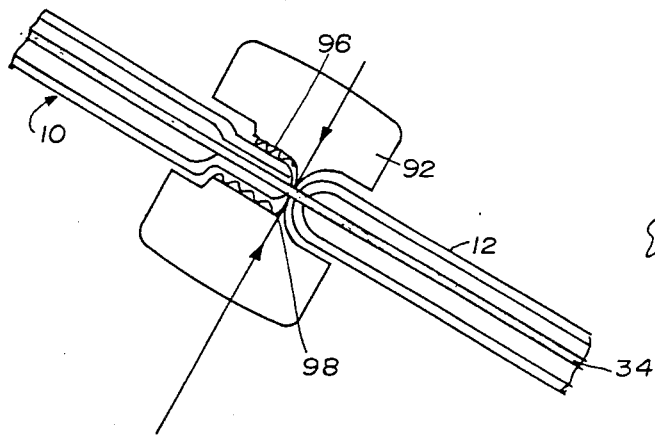
Figure 31:
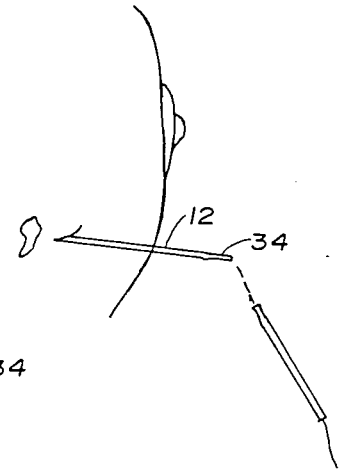

A further accessory which is useful with the present invention is a cutting and crimping device 90 which has particular applicability when an elongated wire 34 is extending from the length within an outer cannula member 12 after the assembly 10 has been locked in position within the body tissue. To reduce the external length of the assembly 10, and to prevent possible complications of the assembly penetrating deeper into the target or other vital structure, a cutting and crimping device having a special compression head 92 is utilized to reduce the diameter of the outer cannula member 12 by compressing the outer cannula member about the wire filament 34. The compression head is complimentary, as shown in FIGS. 29 and 30, and includes a compression area 96 which crimps the outer cannula member about the wire surface and includes a cutting area 98 which will cut the outer cannula member without cutting the central wire 34 therein. This cutting and crimping device 90 permits the use of a long needle and converts it to a very short needle for transport from the radiology area into the operating room as shown in FIG. 31.

The unique localization or pinpointing needle assembly in accordance with the present invention permits the easy locking of the needle assembly into any target area and permits the easy repositioning and advancement of the needle assembly within the target area.

Additionally, the needle assembly provides a novel means for locking the needle assembly within the body tissue, which novel means includes the lateral displacement of a barb into the body tissue and includes a helically screw needle portion attached to the distal end of the outer cannula member to lock the assembly within the target area.

The unique handle and locking means described herein permits the precise placement of the needle assembly within the target area and permits the prompt and efficient displacement of the barb or other means of anchoring the assembly to lock the needle assembly at the target area. The utilization of a needle assembly having a substantial portion of the outer cannula member being flexible is important when using the localization needle assembly in areas of the breast or other targets where there is difficulty compressing the target for X-ray or other filming.

Finally, the remote incisional accessory used in conjunction with the present invention may be used in situations in any part of the body such as remotely placing a catheter into a vessel or where the surgeon would like to make an incision remote from where the needle has been placed within the body for cosmetic and other reasons.

The above-described embodiments illustrates the features of the present invention in a form in which the inventor believes is most practical and suited to his uses, however, other configurations exist which may be generated by persons skilled in the art and such variations are to be considered within the spirit and scope of the present invention and which are claimed as stated below.

We claim:

1. A localization needle assembly for pinpointing lesions within body tissue, including in combination:
   an outer tubular cannula member having a distal end and a proximal end with said cannula member having an opening predeterminedly lcoated from said distal end,
   an elongated inner needle member having a distal end portion and a proximal end portion, said inner needle member having a pointed tip and anchoring means at its distal end portion, said inner needle member being slidably mounted for movement within said outer cannula member between an extended position and a retracted position, and
   said anchoring means having a mounting portion secured to said distal end portion of said inner needle member and a barb portion contained within said outer cannula member and extending towards said opening in said outer cannula member when said inner needle member is in its extended position and said barb portion moved outward of said outer cannula member through said opening predeterminedly located from the distal end of said outer cannula member to engage body tissue when said inner needle member is moved to its retracted position to lock the needle assembly within the body tissue.

2. The localization needle assembly according to claim 1, wherein said anchoring means comprises an elongated member having said barb portion at one end thereof and said pointed tip at the other end thereof, said inner needle member having a cutaway portion spaced inwardly of its distal end portion, said elongated member mounted in said cutaway portion with its tip portion extending beyond the distal end portion of said inner member and its barb portion received within said cutaway portion when said inner needle member is in its extended position and movable out of said cutaway portion and outward through said opening in said outer cannula member when said inner member is moved to said retracted position.

3. The localization needle assembly according to claim 1, wherein said inner needle member includes a cutaway portion spaced inwardly of its distal end portion, which said anchoring means being received within said cutaway portion and having its mounted portion secured thereto, with said barb portion being located within said cutaway portion when said inner needle member is in its extended position and movable out of said outer cannula member when said inner needle member is moved to its retracted position.

4. The localization needle assembly according to claim 3, wherein said pointed tip is formed integrally with said inner needle member.

5. The localization needle assembly according to claim 4, wherein said pointed tip is received in a countersunk opening provided at the distal end portion of said inner needle member and secured thereto.

6. The localization needle assembly according to claim 1, wherein said outer cannula member has a second opening predeterminately located from said distal end and said inner needle member includes further anchoring means having a barb portion contained within said outer needle member and extending toward said second opening in said outer needle when said inner needle member is in its extended position, with said barb portion of said further anchoring means moved outward of said outer cannula member through said further opening to engage body tissue when said inner needle member is moved to its retracted position.

7. The localization needle assembly according to claim 1, wherein said outer tubular cannula member includes a rigid tubular portion and a flexible tubular portion secured to said rigid tubular portion, said inner needle member in its extended position passing through said flexible and rigid portions of said outer tubular cannula member thereby maintaining said flexible portion substantially rigid during insertion of the needle assembly into a body, with said inner needle member being removable from outer cannula member thereby providing flexible needle assembly.

8. The localization needle according to claim 7, wherein the distal end of said rigid portion of said outer cannula member includes a helical tapered screw tip defined thereon.

9. The localization needle assembly according to claim 1, including locking means for locking said inner member to said outer cannula member for preventing relative rotation therebetween.

10. The localization needle assembly according to claim 9, wherein said locking means includes a notch on one of said members at the proximal end thereof and a projection on the other one of said members at its proximal end and engaging said notch to prevent rotation of said inner needle member relative to said outer cannula member when said inner needle member is in its extended portion.

11. The localization needle according to claim 9, wherein said locking means comprises a proximal handle portion engageable with said inner needle member to fixedly lock thereon and a distal handle portion engageable with said outer cannula member to fixedly lock thereon and means coupling said proximal and distal handle portions together.

12. The localization needle according to claim 1 wherein said outer cannula member includes an opening adjacent its proximal end and said inner needle member includes a projection cooperating with said opening to limit travel of said inner needle member between its extended and retracted positions.

13. A localization needle assembly for locating lesions within body tissue, including in combination:
an outer tubular cannula member having a distal end and a proximal end with said cannula member having an opening predeterminedly located from said distal end,
an elongated inner needle member slidably mounted within said outer cannula member and having a distal end portion and a proximal end portion, with said inner needle member having a cutaway portion spaced inwardly of said distal end portion, with said inner needle member being slidably mounted for movement within said outer cannula member between an extended position and a retracted position, and
projections means fixedly mounted to said distal end portion of said inner needle member, said projection means having a forward projection means extending beyond said distal end portion of said inner needle member and a barb portion adapted to be received within said cutaway portion of said inner needle member when said inner needle member is in an extended position and wherein said barb portion is slidably moved outward through said opening predeterminately located from the distal end of said outer cannula member to engage the body tissue when said inner needle member is moved to its retracted position to lock the needle assembly within the body tissue.

* * * * *

UNITED STATES PATENT AND TRADEMARK OFFICE
CERTIFICATE OF CORRECTION

PATENT NO. : 4,799,495

DATED : January 24, 1989

INVENTOR(S) : Irvin F. Hawkins, Jr., George A. Rafferty, Jr., Mark C. Hawkins and Jeffrey S. Hawkins It is certified that error appears in the above-identified patent and that said Letters Patent is hereby corrected as shown below:

Item [75], on the cover sheet, the first inventor's name should be --Irvin F. Hawkins, Jr.--.

Column 8, line 59, change "predeterminely" to --predeterminedly--;

Column 14, line 40, change "which" to --with--;

line 56, change "predeterminately" to --predeterminedly--;

line 59, change "needle" to --cannula--;

line 60, change "needle" to --cannula member--;

Column 15, line 8, after "providing" insert --a--;

line 24, change "portion" to --position--; and

Column 16, line 29, change "predeterminately" to --predeterminedly--.

Signed and Sealed this

Twelfth Day of December, 1989

Attest:

JEFFREY M. SAMUELS

Attesting Officer    Acting Commissioner of Patents and Trademarks